US010765400B2

(12) United States Patent
Blackbourne et al.

(10) Patent No.: US 10,765,400 B2
(45) Date of Patent: Sep. 8, 2020

(54) VASCULAR TARGETING SYSTEM

(71) Applicant: The Government of the United States, as represented by the Secretary of the Army, Fort Detrick, MD (US)

(72) Inventors: Lorne H. Blackbourne, Houston, TX (US); Jose Salinas, Houston, TX (US); Ronald D. Grisell, Fort Sam Houston, TX (US)

(73) Assignee: The Government of the United States, as Represented by the Secretary of the Army, Fort Detrick, MD (US)

( * ) Notice: Subject to any disclaimer, the term of this patent is extended or adjusted under 35 U.S.C. 154(b) by 152 days.

(21) Appl. No.: 15/568,974

(22) PCT Filed: Apr. 25, 2016

(86) PCT No.: PCT/US2016/029192
§ 371 (c)(1),
(2) Date: Oct. 24, 2017

(87) PCT Pub. No.: WO2016/172696
PCT Pub. Date: Oct. 27, 2016

(65) Prior Publication Data
US 2018/0125450 A1 May 10, 2018

Related U.S. Application Data

(60) Provisional application No. 62/152,660, filed on Apr. 24, 2015.

(51) Int. Cl.
A61B 8/00 (2006.01)
A61B 8/08 (2006.01)
(Continued)

(52) U.S. Cl.
CPC ............ A61B 8/0891 (2013.01); A61B 5/489 (2013.01); A61B 8/0841 (2013.01); A61B 8/06 (2013.01)

(58) Field of Classification Search
None
See application file for complete search history.

(56) References Cited

U.S. PATENT DOCUMENTS 4,291,988 A * 9/1981 Dixon, Jr. ............ G01N 21/031
356/437
6,074,382 A * 6/2000 Asah .................... A61B 18/203
606/10
(Continued)

OTHER PUBLICATIONS

Seldinger SI (1953). "Catheter replacement of the needle in percutaneous arteriography; a new technique". Acta radiologica 39 (5): 368-376.
(Continued)

Primary Examiner — Joel F Brutus
(74) Attorney, Agent, or Firm — Leigh Callander

(57) ABSTRACT

An embodiment of the invention provides a method including obtaining ultrasonic images of one or more vessel to be catheterized with an ultrasonic imaging device 212 and identifying the center(s) of the vessel(s) with the ultrasonic images. One of the vessels is punctured with a needle 220 based on the identifying of the center of the vessel. A guide wire 230 is inserted into the vessel and maneuvered with guide wire ultrasonic feedback control. The guide wire ultrasonic feedback control includes obtaining ultrasonic images of the vessel and the guide wire 230 in the vessel, and displaying the ultrasonic images of the vessel and the guide wire 230 in the vessel to a user. A catheter sheath 240 is inserted over the guide wire 230 and maneuvered with sheath ultrasonic feedback control. The guide wire 230 is removed and a catheter 250 is inserted into the catheter
(Continued)

sheath 240 and maneuvered with catheter ultrasonic feedback control.

20 Claims, 9 Drawing Sheets

(51) Int. Cl.
*A61B 5/00* (2006.01)
*A61B 8/06* (2006.01)

(56) References Cited

U.S. PATENT DOCUMENTS

| | | | |
|---|---|---|---|
| 6,132,379 A | 10/2000 | Patacsil et al. | |
| 8,257,265 B1* | 9/2012 | Raju | A61B 8/0891 600/437 |
| 2006/0184029 A1 | 8/2006 | Haim et al. | |
| 2008/0249467 A1 | 10/2008 | Burnett et al. | |
| 2010/0010505 A1* | 1/2010 | Herlihy | A61B 90/11 606/130 |
| 2012/0095339 A1* | 4/2012 | Tashiro | A61B 8/4427 600/443 |
| 2012/0157854 A1 | 6/2012 | Kurrus et al. | |
| 2012/0197357 A1* | 8/2012 | Dewey | A61B 18/203 607/89 |
| 2012/0211006 A1* | 8/2012 | Gill | A61B 34/30 128/200.26 |
| 2012/0259219 A1 | 10/2012 | Sheldon et al. | |
| 2013/0131597 A1 | 5/2013 | Blaivas et al. | |
| 2013/0281787 A1* | 10/2013 | Avneri | A61M 25/0133 600/208 |
| 2015/0011887 A1 | 1/2015 | Ahn et al. | |

OTHER PUBLICATIONS

Higgs ZC, Macafee DA, Braithwaite BD, Maxwell-Armstrong CA (2005). "The Seldinger technique: 50 years on". Lancet 366 (p4p4): 1407-1409.

Schummer W, Schummer C, Gaser E, Bartunek R (2002). "Loss of the guide wire: mishape or blunder?". British journal of anaesthesia 88 (1): 144-146.

Stannard A, Eliason JL, Rasmussen TE. (2011) Resuscitative Endovascular Balloon Occlusion of the Aorta (REBOA) as an Adjunct for Hemorrhagic Shock. J. Trauma; 71(6):1869-1872.

Stone MB, Nagdev A, Murphy MC, Sisson CA.(2008). Ultrasound detection of guidewire position during central venous catheterization. Am J Emerg Med. Jan. 2010;28(1):82-84.

Bodenham, Reducing major procedural complications from central venous catheterisation, Journal of the Association of Anaesthetists of Great Britain and Ireland, 2011, 66, pp. 6-9.

Lalu, M. M.; Fayad, A; Ahmed, O; Bryson, G. L; Fergusson, D. A.; Barron, C. C.; Sullivan, P; Thompson, C; Canadian Perioperative Anesthesia Clinical Trials Group (2015). "Ultrasound-Guided Subclavian Vein Catheterization: A Systematic Review and Metaanalysis". Critical Care Medicine: 1, pp. 1498-1507.

International Search Report and Written Opinion of the International Search Authority for PCT/US2016/029192, dated Jul. 27, 2015, pp. 1-11.

* cited by examiner

VASCULAR TARGETING SYSTEM

This is a U.S. national stage of PCT Application No. PCT/US2016/29192 filed on 25 Apr. 2016 in the U. S. Patent and Trademark Office, which claims the benefit of U.S. Patent Application Ser. No. 62/152,660 filed on 24 Apr. 2015, the entireties of which are incorporated herein by reference.

This invention was made with government support under Contract No. W81XWH-11-D-0027 awarded by the U.S. Army Institute of Surgical Research, Fort Sam, Houston. The government has certain rights in the invention.

FIELD OF THE INVENTION

The present invention relates to a vascular targeting system, and more specifically, to methods, systems, devices for direction of a needle or trocar to make an incision into the lumen of a selected blood vessel.

BACKGROUND

Ultrasonic imagery used to locate blood vessels may detect both arteries and veins. Often the imagery is obscured by numerous false reflections and shadows in the ultrasound image, which can complicate the interpretation of the elliptical cross-sections of the vessels.

With hemorrhage cases, intervention should be as rapid as possible at the site where the patient is injured. This includes slowing down the rate of blood loss to a body region such as chest, abdomen, and legs. There is also need for safer and accurate central line catheterization, which maintain blood pressure and administer medications through the carotid or the femoral vein. Currently however, untrained medical personnel are often reluctant to attempt an incision into the blood vessel. A device currently used contains multiple needles aligned in a row, to be inserted manually and aimed blindly in the general direction of the blood vessels; the idea being that one of the needles is likely to enter a desired blood vessel. However, given the bulk of the apparatus, it would be difficult to continue the Seldinger technique, after needle incision, for insertion of a balloon catheter. There is also some danger that the vessel will be damaged, or that the needle will pass through. When a needle is inserted without guidance there is a chance that the needle may graze the vessel, breaking it open and causing internal bleeding which can only be stemmed by time-consuming surgery to suture the vessel before another insertion can be attempted. Unless a needle enters approximately into the center of a vessel, there is a chance of damage to the vessel by subsequent application of trocars, dilators (tubes to guide a catheter) and the catheter. With central venous catheterization, it is a danger that the tip of the catheter is inserted into the wrong vessel. In the case of carotid insertion of a central line, catheters have been placed in the carotid artery or the vertebral artery; and in the case of groin insertion, into the common femoral artery instead of the femoral vein Nevertheless, a significant fraction of battlefield deaths are due to hemorrhage before medical procedures can be taken such as use of a tourniquet, so a speedy and accurate insertion of a catheter can essential to survival while the patient is transported to surgery. There is also need for safer placement of other catheters such as a central venous catheter and a peripherally inserted central catheter or "PICC line".

SUMMARY OF THE INVENTION

At least one embodiment of the invention provides a method including obtaining ultrasonic images of one or more vessel to be catheterized with an ultrasonic imaging device and identifying the center(s) of the vessel(s) with the ultrasonic images. The center(s) of the vessels are identified with a processor. One of the vessels is punctured with a needle based on the identifying of the center of the vessel.

A guide wire is inserted into the vessel and maneuvered with guide wire ultrasonic feedback control. The guide wire ultrasonic feedback control includes obtaining ultrasonic images of the vessel and the guide wire in the vessel, and displaying the ultrasonic images of the vessel and the guide wire in the vessel to a user. A catheter sheath is inserted over the guide wire and maneuvered with sheath ultrasonic feedback control. The sheath ultrasonic feedback control includes obtaining ultrasonic images of the vessel and the catheter sheath in the vessel, and displaying the ultrasonic images of the vessel and the catheter sheath in the vessel to the user. The guide wire is removed and a catheter is inserted into the catheter sheath and maneuvered with catheter ultrasonic feedback control. The catheter ultrasonic feedback control includes obtaining ultrasonic images of the vessel and the catheter in the vessel, and displaying the ultrasonic images of the vessel and the catheter in the vessel to a user. The operator then proceeds with what is commonly known as the Seldinger Technique. At any point during initial insertions of surgical components into a vessel, the ultrasonic imagery provides visual feedback.

BRIEF DESCRIPTION OF THE DRAWINGS

The present invention is described with reference to the accompanying drawings. In the drawings, like reference numbers indicate identical or functionally similar elements.

DETAILED DESCRIPTION

Example, non-limiting, embodiments of the present invention are discussed in detail below. While specific configurations are discussed to provide a clear understanding, it should be understood that the disclosed configurations are provided for illustration purposes only and elements of different components can be switched with other similar components. A person of ordinary skill in the art will recognize that other configurations may be used without departing from the spirit and scope of the invention.

Figure 1:
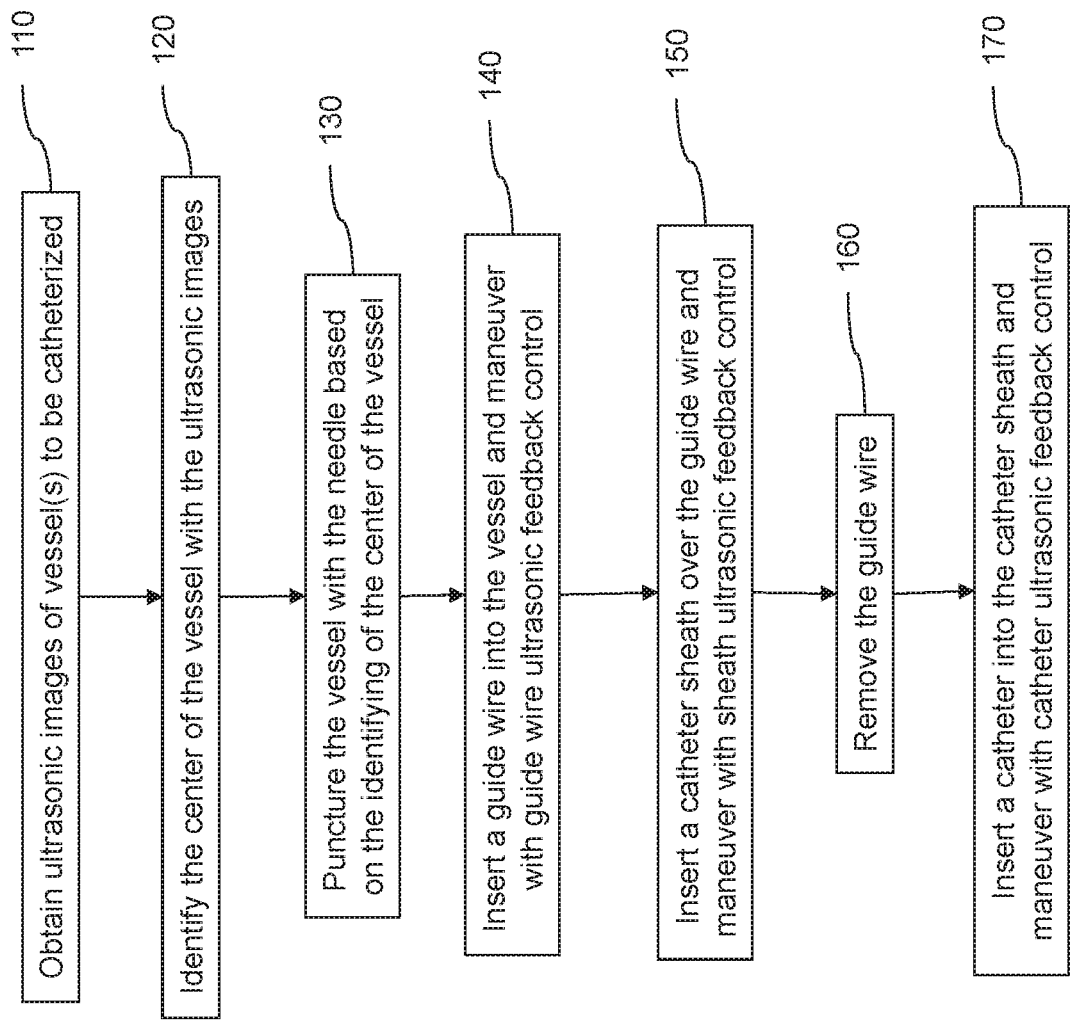
FIG. 1 is a flow diagram illustrating a method for the control software for a laser pointing system for illuminating a spot where the incision can be made and indicating the angle of insertion of the needle according to an embodiment of the invention.

FIG. 1 is a flow diagram illustrating a method for the control software for a laser pointing system for illuminating a spot where the incision can be made and indicating the angle of insertion of the needle according to at least one embodiment of the invention. Ultrasonic images of one or more vessels to be catheterized are obtained with an ultrasonic imaging device 110. This can include positioning a probe of the ultrasonic imaging device on a skin surface over the vessel(s). More specifically, in at least one embodiment, an appendage of a patient (e.g., thigh) is scanned with the ultrasonic imaging device to generate ultrasonic images of the appendage; and, the ultrasonic images of the appendage are automatically analyzed by a processor (also referred to herein as the "algorithm" or the "ultrasonic image interpretation algorithm") to identify the vessel. The ultrasonic images can include one or more cross-section images of the vessel.

Using the ultrasonic images, the processor identifies the center of the vessel 120. In at least one embodiment, a laser pointer emits a laser onto the skin surface of the appendage to designate a puncture point for a needle, where the position of the puncture point is based on the identifying of the center of the vessel. The needle punctures the vessel based on the identifying of the center of the vessel 130.

A guide wire can be inserted into the vessel and maneuvered with guide wire ultrasonic feedback control 140. The guide wire ultrasonic feedback control can include obtaining ultrasonic images of the vessel and the guide wire in the vessel with the ultrasonic imaging device, and displaying the ultrasonic images of the vessel and the guide wire in the vessel to a user on a display on or connected to the ultrasonic imaging device. As used herein, the term "connected" includes operationally connected, logically connected, in communication with, physically or wirelessly connected, engaged, coupled, contacts, linked, affixed, and attached.

A catheter sheath can be inserted over the guide wire and maneuvered with sheath ultrasonic feedback control 150. As used herein, the term "ultrasonic feedback control" includes control under automated system guidance, and under manual control by the user guided by visual feedback. The sheath ultrasonic feedback control can include obtaining ultrasonic images of the vessel and the catheter sheath in the vessel with the ultrasonic imaging device, and displaying the ultrasonic images of the vessel and the catheter sheath in the vessel to the user.

In at least one embodiment, the guide wire is removed 160; and, a catheter is inserted into the catheter sheath and maneuvered with catheter ultrasonic feedback control 170. The catheter ultrasonic feedback control can include obtaining ultrasonic images of the vessel and the catheter in the vessel with the ultrasonic imaging device, and displaying the ultrasonic images of the vessel and the catheter in the vessel to a user.

In at least one embodiment of the invention, the amount of force applied to the guide wire, the catheter, and/or the sheath is measured; and, an audible alert and/or a visual alert is generated when the measured amount of force exceeds a predetermined threshold. The processor can analyze the ultrasonic images to identify when the catheter reaches a predetermined distance from the puncture point; and, a balloon of the catheter can be automatically inflating when the catheter reaches the predetermined distance from the puncture point.

In addition, the rate of blood flow in the vessel can be measured; and, the amount of air in the balloon of the catheter can be adjusted based on the measured blood flow. Blood flow can be approximated for roughly annular orifices using the Bernoulli equation. A pressure differential across a balloon can be measured by pressure sensors above and below the balloon. In one embodiment, the diameter of the shaft of the catheter above the upper balloon is smaller than the diameter of the shaft below the balloon, so there are two different cross sectional areas above and below. Similarly the shaft below the lower balloon can be larger (or smaller) than the shaft above. The equation for the mass flow rate can be a function of the square root of the pressure difference, the areas above and below a balloon, and mass density of the blood.

When the measured blood flow is high, the amount of air in the balloon can be increased to prevent hemorrhage distally to the balloon. The processor can control the balloon pressure based on blood pressure sensed. Occasionally the balloon can be deflated slightly to allow more blood flow into a compartment (e.g., chest, leg) to minimize tissue damage. The balloon may expand only if its internal pressure is slightly higher than the down steam blood pressure. The air pump connected to the balloon can temporarily increase the internal pressure until the measured downstream pressure is as desired according to the controller's algorithm. When the measured blood flow is low, the amount of air in the balloon can be decreased to allow enough blood into the distal compartment.

The processor can analyze the ultrasonic images to measure the distance between the tip of the guide wire, the catheter, and/or the sheath and a vessel wall of the vessel, and generate an audible and/or visual alert when the measured distance between the tip and the vessel wall falls below a threshold distance. The processor can also analyze the ultrasonic images to measure the distance between the balloon of the catheter and the vessel wall of the vessel, and generate an audible and/or visual alert when the measured distance between the balloon and the vessel wall falls below a threshold distance.

In at least one embodiment of the invention, a spot on the skin is illuminated by means of a directable laser where the needle can be inserted; and, the needle is aligned in parallel with the laser's beam. The illuminating of the spot on the skin can be performed by means of a laser mounted in fixed position relative to the ultrasound beam, which can swivel to allow the laser to be directed by means of motors at a spot on the skin where the needle should be inserted. The direction angles of the laser can be controlled by motors which aim the laser's beam at the interior of the selected vessel at the plane of the cross-section. Moreover, the direction angles of the laser can be controlled by software operating on a processor (or other programmable device), which controls motors to aim the laser's beam at the interior of the selected vessel at the plane of the cross-section. The software can compute the angles by which the motors should direct the laser, and can convert the computations from digital form to analog form suitable to drive the motors. The motors, for example, can be Selsin motors or a type commonly known as linear motors.

At least one embodiment of the invention initiates the location of arteries and/or veins by intersecting horizontal and vertical lines through peaks of marginal histogram intensities, wherein a horizontal line passes through the peak of a margin histogram, latter summing image intensities across each row, and wherein a vertical line passes through a peak in the marginal histogram which sums intensities across each column of the image. In another embodiment, diagonal lines are intersected with the vertical and horizontal lines to disambiguate the positions, in horizontal and vertical coordinates or dimensions, wherein the diagonal lines pass through a marginal histogram which sums image intensities along each diagonal line.

It can be determined which candidate intersections of the lines are most likely to be one of several possible combinations occurring in a groin area: vein and artery, two veins and one artery, one vein and two arteries, and two veins and two arteries. All of the combinations can be possible identifications by the imaging algorithm depending on how far above or below the groin crease and the interlingual crease the user has placed the ultrasonic probe. The locations used to direct the user to move the probe upwards, toward the head, or downwards, since both the artery and vein have bifurcations near the crease, whereas it is desired to insert the needle and trocar into a vessel above its bifurcation to allow ease of insertion of the catheter.

The rules can rely on the vein or its bifurcations to lie skin-ward, whereas the artery or its bifurcations can lie deeper into the groin. Depending on which crease is being accessed by the probe (e.g., left leg or right leg), the arteries can lie to the inside of the leg relative to the veins. Additional rules can depend on Doppler signals from the vessels, wherein blood flow toward the leg can be in an artery, and wherein blood flow toward the abdomen can be flow in a vein.

It can be determined whether the imaged vessel compresses into an elliptical shape by compression of an imaged vessel with the hand or finger over the groin. The imaged vessel can be determined to be a vein when the imaged vessel is compressed; and, the imaged vessel can be determined to be an artery when the imaged vessel is not compressed.

Figure 2:
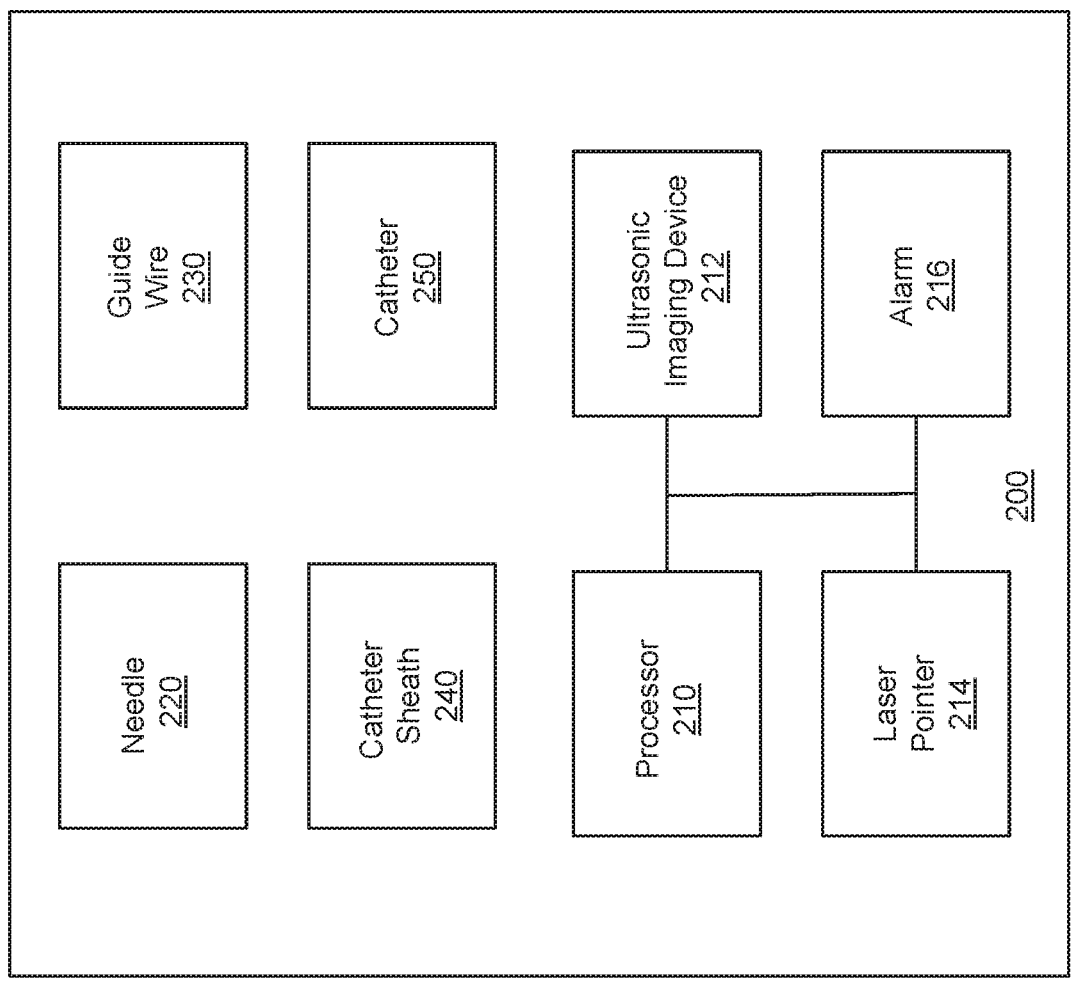
FIG. 2 is a diagram illustrating a system for the guidance of a needle or trocar according to an embodiment of the invention.

FIG. 2 is a diagram illustrating a system 200 for the guidance of a needle or trocar according to at least one embodiment of the invention. The system 200 includes a processor 210 that can identify the center of a vessel to be catheterized from ultrasonic images obtained from, for example, an ultrasonic imaging device 212. In an alternative embodiment, the ultrasonic image is provided by an external source. A needle 220 can puncture the vessel based on the identification of the center of the vessel by the processor 210; and, a guide wire 230 can be inserted into the vessel and maneuvered with guide wire ultrasonic feedback control. The guide wire ultrasonic feedback control can include ultrasonic images of the vessel and the guide wire 230 in the vessel.

A catheter sheath 240 can be inserted over the guide wire 230 and maneuvered with sheath ultrasonic feedback control, wherein the sheath ultrasonic feedback control can include ultrasonic images of the vessel and the catheter sheath 240 in the vessel. A catheter 250 can be inserted into the catheter sheath 240 and maneuvered with catheter ultrasonic feedback control, wherein the catheter ultrasonic feedback control can include ultrasonic images of the vessel and the catheter 250 in the vessel.

An ultrasonic imaging device 212 can be connected to the processor 210, wherein the ultrasonic imaging device can obtain ultrasonic images of the vessel to be catheterized, the needle 220, the guide wire 230, the catheter sheath 240, and/or the catheter 250. The ultrasonic imaging device 212 can obtain at least one cross-section image of the vessel. The ultrasonic imaging device 212 can scan an appendage of the patient to generate ultrasonic images of the appendage, wherein the processor 210 can analyze the ultrasonic images of the appendage to identify the vessel.

The system 200 can also include a laser pointer 214, wherein the laser pointer 214 can emit a laser onto a skin surface to designate a puncture point for the needle 220, and wherein the position of the puncture point can be based on the identification of the center of the vessel by the processor 210.

The processor 210 can measure the amount of force applied to the guide wire 230, the catheter 240, and/or the sheath 250 (e.g., with a force sensor). The system 200 can further include an alarm 216 connected to the processor 210, the alarm 216 generates at least one of an audible alert and a visual alert when the measured amount of force exceeds a predetermined threshold as determined by the processor 210. The processor 210, ultrasonic imaging device 212, laser pointer 214, and/or alarm 216 can be integrated onto a single device. In another embodiment, the processor 210, ultrasonic imaging device 212, laser pointer 214, and/or alarm 216 can be located on separate (yet connected) devices within the system 200.

The processor 210 can analyze the ultrasonic images to identify when the catheter 250 reaches a predetermined distance from the puncture point, and can automatically inflate a balloon of the catheter 250 when the catheter 250 reaches the predetermined distance from the puncture point. The processor 210 can adjust the amount of air in the balloon of the catheter 250 based on measured blood flow.

The processor 210 can analyze the ultrasonic images to measure the distance between the tip of the guide wire 230, the catheter 250, and/or the sheath 240 and a vessel wall of the vessel. The alarm 216 can generate an audible and/or visual alert when the measured distance between the tip and the vessel wall falls below a threshold distance. The processor can also analyze the ultrasonic images to measure the distance between the balloon of the catheter 250 and the vessel wall of the vessel. The alarm 216 can generate an audible and/or visual alert when the measured distance between the balloon and the vessel wall falls below a threshold distance.

At least one embodiment of the invention provides a vascular targeting system (also referred to herein as the "system", "device", or "instrument") that includes an ultrasonic guide for the insertion of a needle and/or trocar into a selected vessel, followed by the insertion of a catheter through the needle incision. An ultrasonic probe can provide video imagery to an algorithm which processes the video to identify one or more vessel outlines (estimates of outer and inner vessel walls) to indicate where the approximate vessel center is located. As used herein, the term "algorithm" includes computer program instructions that may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the computer program instructions. The vessel center can then be the aim point for the needle which makes the initial incision for placement of a catheter (e.g., according to the Seldinger technique). To further assure the accuracy of insertion, a laser targeting system can take coordinates from the ultrasonic imaging and direct a laser beam at the exact spot for insertion with the exact angle. The system can assist medical personnel in accurately locating the wall of the vessel to be punctured. In at least one embodiment, coordinates of the blood vessel center are transformed to two direction angles of the laser, vertical and side-to-side, using a computation given distance of the probe from the vessel (echo delay), and height of the laser's pivot point above the beam, and its offset from the transducer surface. The computation can provide the laser angles so as to complete a side of a scalene triangle given the known sides which are given by these dimensions.

In at least one embodiment, the laser targeting system computes coordinates of the vessel center from information provided by the ultrasonic image interpretation algorithm to control the pointing of a laser to orient the medical personnel to the correct insertion of a needle or trocar through the vessel wall.

In addition to providing a laser beam to aim the needle or trocar to make the initial incision, the system can monitor insertion of the catheter following the incision. It also can assist in assessing any significant blood loss when the catheter is removed, provide ultrasonic imagery to help in the decision to perform surgery if necessary, to close the vessel wound, and in some cases to remove the catheter by other approaches.

While the ultrasonic probe can be separate from the laser targeting system, in at least one embodiment the probe and laser are contained in an integrated unit with a pistol grip for ease of use. In at least one embodiment, the system assists the medical personnel in preparing the incisions for the catheter, first by confirming the position for the incision by illuminating the point on the skin for insertion via a laser beam, and second, by indicating the direction from that point on the skin into the vessel by means of the angle between the laser and the target point on the skin. Thus, the display can provide directions for alignment and/or the angle of insertion. The needle, as well as an optional sheath, and then the catheter, can be inserted along the direction of the laser beam and through the point on the skin into the vessel. In at least one embodiment, there is provided a trigger or button on the grip which turns on the ultrasonic probe and laser, and the computer controller also contained within the unit. A small screen on the instrument (also referred to herein as the "device" or "unit") can display the ultrasonic imagery. The unit can aid considerably under austere conditions at the site of a civilian casualty or on a battlefield. Data from the site of injury can be forwarded to transports or rearward treatment facilities including a receiving hospital.

Once the center of the desired vessel has been identified, the operator may proceed to insert a needle or trocar at a point near the head of the probe and in the angle with which the probe is held. Tracking of the needle as it is inserted can be initiated by the system, and this can be displayed on the screen.

Both the needle or trocar and the targeted lumen should be in plain view, otherwise the system can warn the user by a signal such as a yellow color on the instrument's screen. A red color can indicate that it is dangerous to proceed with the incision in the direction being taken. This can aid highly distracted or inexperienced personnel. A green color can indicate that it is safe to proceed with the incision into the vessel. The instrument and image processing can continue to monitor the progress of various stages of operations near or under the probe head. The probe can remain held steady in one position throughout, unless there is an error condition which indicates that an ultrasonic exam should be made at another point. Thus, the alerts can significantly improve the operation safety, and can make the instrument useful under possible extreme conditions of field operations. The processor can include a set of rules to make decisions regarding vessel selection.

The following provides a summary of an example deployment of a catheter according to an embodiment of the invention, such as a central line catheter. Location of the approximate center of the vessel can be determined via segmentation of imagery of the vessel cross-section, once good quality images are attained. A sharp hollow needle to puncture the given artery can be aligned, aiming for the center of the artery. A guide wire can be inserted into the needle bore and into the vessel with ultrasonic imaging feedback. The needle can be removed while clamping the guide wire into place, again with ultrasonic feedback. A needle, small lance, or trocar can be advanced to make a small incision at the point of puncture. The needle can be retracted and the guide wire can be left in place.

A catheter sheath can be inserted over the guide wire to aid in positioning the catheter. In some cases, a dilator can be inserted in the tip of the sheath to smoothly grade the tip to the guide wire. The sheath can be fed into the vessel via imaging feedback to indicate the progress into the vessel. Optional drainage tube(s) can be inserted as well. The guide wire can be withdrawn once the sheath is in place. The catheter can be advanced into the sheath and into the vessel with ultrasonic feedback control. Additional steps in the catheter deployment can include inflating the balloon(s) if it is a REBOA catheter, deflating or re-inflating REBOA balloons sufficiently to control blood pressure, and/or final deflation of any balloons and withdrawal of the catheter.

In at least one embodiment of the invention, the algorithm includes three components: image processing for interpretation of the ultrasonic imagery; a rule-based system to identify an artery versus a vein, since in some portions of the body such as the groin area there are several vessels including both arteries and veins; and, tracking of a vessel once identified and acquired. The vessel imagery may be obscured by numerous false reflections, shadows, and/or noise in the ultrasound image, which can complicate the interpretation of the roughly elliptical cross-sections of the vessels. The algorithm can apply image processing to remove the artifacts and to clearly identify the vessel walls in many cases. If the imagery is highly noisy, such identification may not be certain, and the operator may be alerted by a warning message, flashing box, and/or by other means on a display screen.

Rules can decide which of one or more outlines represent a cross-section of the desired vessel. For example, one set of rules decides that imagery is of poor quality, no vessel is in view, the outline is probably the wrong vessel (e.g., too small, etc.). Each rule will have available, prior to its execution, the image-processed outline of vessel walls obtained from the ultrasonic video imagery in the field of view of the instrument. The outline of a vessel consists of two curved lines extracted by segmentation of portions of its outer and inner walls where there is sufficiently strong reflection of the ultrasonic pulses of the beam. In good imaging conditions where few artifacts of tissue appear in the vicinity of the vessel, obscuring it, curves will approximately follow the inner and outer surfaces of the vessel wall in the image.

Ultrasound may not reflect off of boundaries that are almost parallel to its beam, so if there is noise or not a clear vessel due to extraneous reflections or other artifacts, the reflections from the inner and outer walls of the vessel in a nearly perpendicular direction to the beam may be too weak to detect. Therefore the curves following the inner and outer vessel walls in a particular frame of the imagery may be fragmented, e.g., only curves following the walls closest to the instrument may be extracted as definite vessel boundaries. Typically, there will be a strong reflection from a relatively short section of the outer wall and another strong reflection from a short sector of the inner wall farthest from the instrument, but the sides of the vessel will be very weak or indistinct. So the preference in the rule processing for vessel walls is to decide vessel or no vessel depending mainly on these two sectors of strong reflection, if it is indeed a vessel. Unlike previous methods, the recommendation is, if there are weak reflections from the perpendicular sides of a putative vessel, to not attempt to estimate a "diameter" perpendicular to the beam, but only to measure the distance between "top" (nearest) and "bottom" (farthest) average curve locations. If a perpendicular diameter is reasonably "certain", then both can be used in the rule to decide if this is a vessel; since a vein is not likely to "collapse" so much that the one diameter is not within about half of the other. As a "rule of thumb" and as a part of the vessel rule, if these diameters are grossly out of range of typical veins in the body region of interest, here the groin, then the rule predicts that the extracted curves are not "likely" to indicate a vessel.

In the rule here, and most other rules, these logical thresholds are statistically estimated, given many images of blood vessels, preferably thousands, so that reasonable statistics can be obtained about what is an average diameter for an artery in the body region, for example, and what are the ranges of diameters of veins. Generally, the rules use thresholds which are, given the noise distribution, one or two standard deviations above the average for the extracted feature. These give a reasonable estimate for "certainty", i.e. that the null hypothesis, e.g. that this is not a vein, or this is not an artery, can be rejected correctly about 90 to 95 percent of the time.

Following similar structure, other rules determine relative positions of putative veins and arteries, where the relative vertical and horizontal distances (along the body line under the probe) are again estimated to be above or below thresholds determined by statistics, but here there are additional considerations depending on the patient's body type. For example, the patient's fat layer above the vessels may be such and so, by direct estimation. More difficult is the decision as to whether the reflections are due to a large muscle and its fascia which lies just above the vessels. In the latter case, a muscle size estimate can be input to the system to help in its decision making. Further "evidence" can include Doppler measurements, which add certainty, again in the precise sense of statistical variability and physiological variation. Thus, if the Doppler frequency shift is higher than the fundamental frequency of the instrument, then it is "likely" that blood is flowing toward the instrument in the putative vessel. Hence in the groin, this is more likely to be an artery. On the other hand, if the frequency shift is below that transmitted, then the structure is more likely to be a vein. In addition to identifying the vessel, the rules may advise the operator as to where to move the probe in general terms, such as "move left or upwards" until two vessels are seen, as in the upper groin where there is one large vein and one large artery.

Further rules can come into play when additional evidence has been obtained. For example, when the system is used to aid the insertion of a central line catheter or a REBOA catheter, the operator may depress the skin over the suspected vein while viewing the imagery to see if the vessel compresses. If it compresses, a rule can take this further evidence into account to decide that this is a vein. If not compressed by a certain extent, the vessel can be ruled to be an artery and suitable (e.g., for insertion of a REBOA catheter). The rules can also employ Doppler ultrasound to further distinguish veins from arteries, which are often seen in close spatial relationship. Thus, the rule-based portion of the algorithm can take into account these various possibilities to identify a vessel and to predict a location at approximately the center of its lumen, ideally with high certainty.

Once acquired by the rules, tracking can commence by means of a specialized tracking algorithm. Tracking can assist in situations where the operator inadvertently jerks the probe or the patient moves, gasps, violently contorts, etc. Tracking can also assist when the noise level abruptly increases so that the vessel is no longer identifiable with certainty. In at least one embodiment, a tracking and fusion algorithm is provided where, even when not seen, the algorithm continues to predict where the vessel may be found, and reacquires the vessel near a predicted location. A vessel may also deform from time to time. For example, an artery may clot or form an embolus, there may be a sudden loss of pressure in a vein, or a spasm or flexion of the extensor muscle above the vein may occur.

The tracking algorithm can be a recursive or time-lagged filter capable of predicting discontinuous motion and missing data. To do this, the tracking algorithm can keep track of several possible models of vessel wall motion simultaneously, with selection of one model as the current best estimate which is the smoothest fit in the high-dimensional space of vessel outline parameters. This can include a particular application of deformation theory of curves. As several models begin to approach in terms of a metric of fit of vessel shape models (mean-squared error), then a playoff can be made between the competing candidates. This can be implemented using the method of Markov transition transitions, whereby sufficient evidence can be accumulated to predict probabilities of transitions between one model being the best choice and another. Another method can track vessel walls as smooth functions based on mathematics of fiber bundles, which can be ideally suited to these models.

The vessel walls can be thought of as stretched out linearly as functions of one variable (e.g., the distance from a central point as a function of angle; in polar coordinates). The algorithm can first break up each competing model function into short pieces. This can help because models may cross over or intersect in complicated ways, so the algorithm can start by breaking the curves into pieces or edges to be integrated as follows. Only a few pixels of length of an edge may suffice (e.g., just long enough that inherent noise does not create largely random edges). The resulting space of edges can be known as a one-dimensional fiber bundle. At a first stage, connections or links can be set up between nearby edges; however, continuity of slopes between neighboring pieces may not be required at this point. The algorithm can thus aim to construct continuous curves through all the edges (but not necessarily smooth). Incidentally, such a line can be considered a "cross-section" of the fiber bundle. Next, large continuous integrations of such pieces can be ranked. These can generally be extended discontinuously some distance beyond their contiguous ends to form a cross-section, possibly somewhat discontinuous, with short but allowable gaps. The cross-sections can then be ranked by continuous length and discontinuities. Following this, another phase of the algorithm can commence to smooth the highest ranked ones, i.e., by filtering noise and estimating their second differences (discrete approximations of curvatures). The filtered sections can be re-ranked and selection of those of the highest rank can be made based on integrals of the absolute values of their curvatures and gaps of any discontinuities. Similar measures of smoothness may apply as well. Ties can be broken by considering closeness of each competing model's curve to the preceding best model, at the previous time iteration. A complication can arise which may be typical of tracking and fusion approaches: sometimes due to noise, clusters of nearby models can form which cannot be competed and eliminated down to one, i.e., there can be unresolvable ties. In this case, the algorithm can branch into a state where it considers all models in the cluster at each time point. To prevent memory from running out, the algorithm can prune the branches back two or three levels. With less bushiness of the graph of branches, more levels can be retained in memory at a reasonable computation rate. But due to incessant noise in these images, only two or three may be maintained because beyond that, the ancestry of branches can recede into the noise.

Any of these pruning algorithms can suffice in this last stage of the tracker, or other similar tracking-and-fusion algorithms. A much smoother and more certain progression of models (the fibers or cross-sections of the fiber bundle) can be obtained in time; and, jumps from one vessel outline to a quite different model can be less chaotic than a Markov approach, which may not take ancestry into account and can depend highly on statistics. The fiber bundle approach may not depend on statistics to a large extent except in smoothing. It can sidestep by using what may also be described as an integrative or holistic approach using a basic method in the field of topology, and thus can be a non-parametric method. It can advance the state of the art in tracking and fusion algorithms.

Figure 3:
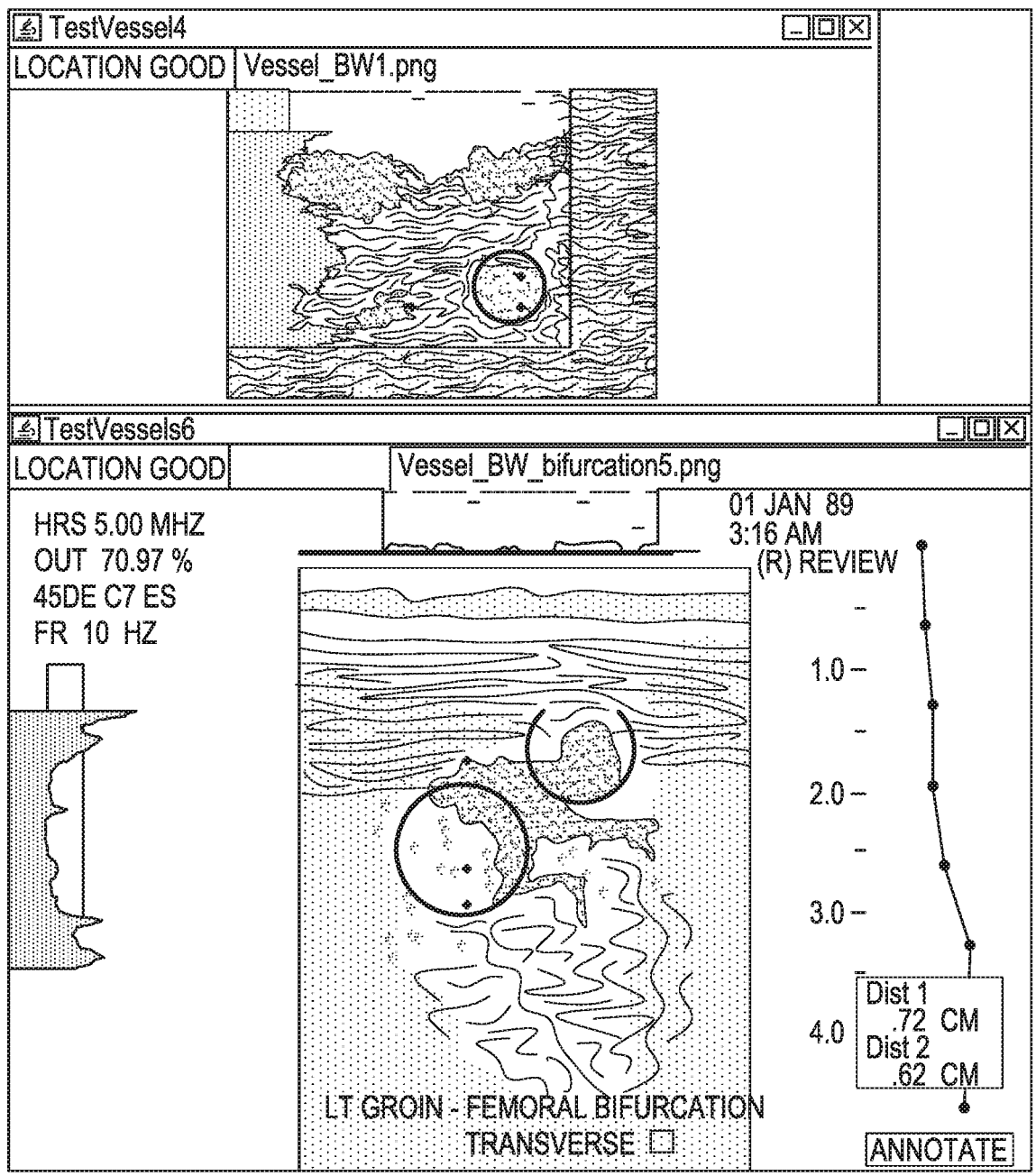
FIG. 3 illustrates an image processing system identifying an actual iliac artery and vein according to an embodiment of the invention.

FIG. 3 illustrates a system identifying an actual iliac artery and vein according to an embodiment of the invention. Properly aligning the probe and surgical components can depend on positively identifying cross-sections of vessels in the area of possible catheter insertion. Shown in FIG. 3 are both arteries and veins at a cross-section below a point in the groin where they both have bifurcated. Thus, there are four different vessels identified by an image segmentation algorithm or segmenter. The segmenter can locate candidates by means of histograms of intensity both horizontally (yellow) and vertically (white) to the left and top, respectively. Minima in these histograms can be where the image is particularly dark, which can likely be a blood vessel. The candidate locations can be at the intersections of horizontal and vertical lines through these minima (white lines for the vein at lower left). These images can be typically quite noisy, so that now the candidates can be evaluated for model-fitting of annular models. Such a model can consist of a lighter ring for the annulus, to fit the vessel wall, and a dark region in the circular region inside the annulus. Rules can be applied in the final stage of identification. For example, if two vessels are identified, then an artery usually appears to the upper left and a vein to the lower left. There can be a number of other rules that handle the various cases, e.g., only one vessel seen, three vessels (a likely bifurcation of one), four vessels (bifurcation of two vessels as seen in the lower groin). Such rules can serve to advise the operator about where to move the probe if correct vessels are not imaged.

For example, if a non-bifurcated iliac artery and vein are not positively identified (or as predicted by the tissue model for another region of application of the device) then an advisory message is generated to the operator to move the probe above or below the initial location when attached to the body area until a sufficient fit of the imagery to the model's geometry is obtained to positively identify the vessel for insertion. The probe can then be moved upwards in the groin area away from the bifurcations so that only one vein and one artery are identified.

In at least one embodiment, doppler mode can be used to more positively identify the artery and vein since blood flow is opposite for these vessels; however, Doppler flow measurements may not be necessary given good segmentation of the vessel cross-sections, so this may not be used apart from image segmentation.

Figure 4:
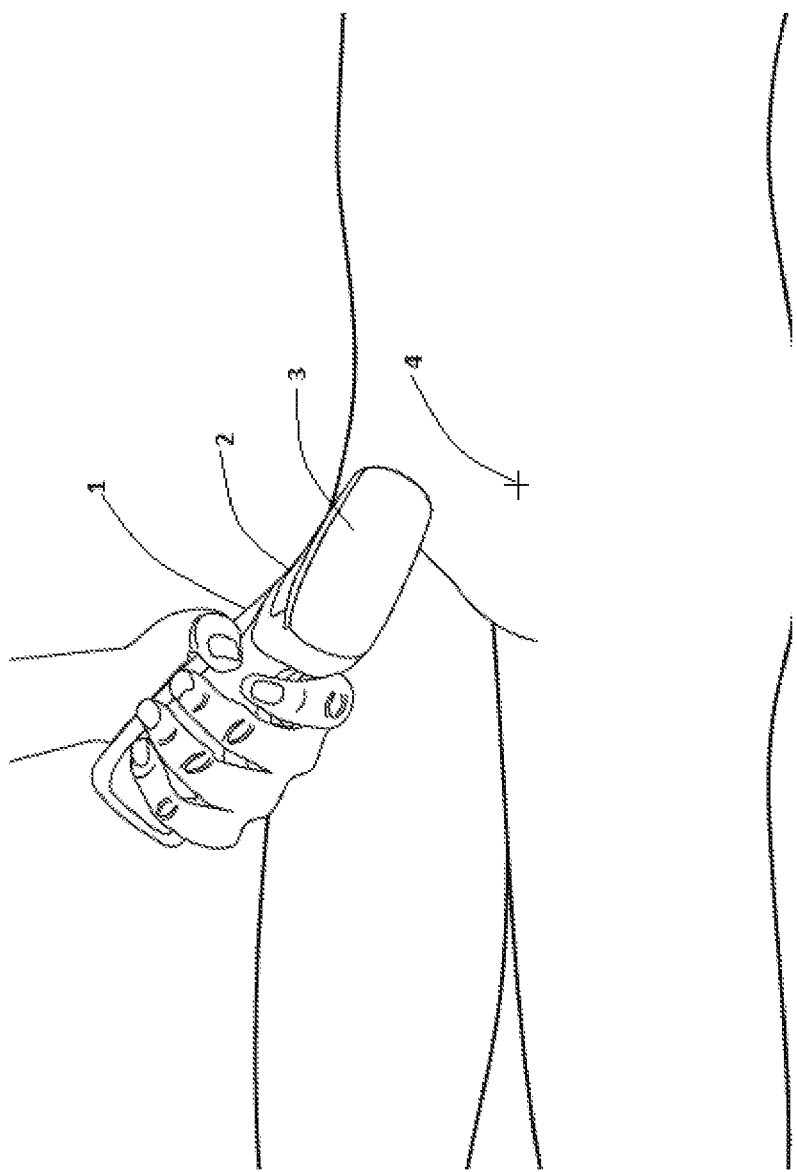
FIG. 4 illustrates the system in use with a prone patient according to an embodiment of the invention.

FIG. 4 illustrates the system in use with a prone patient according to an embodiment of the invention, where a probe is approaching the groin area where a catheter is to be inserted. The convenient pistol grip 1 can be swiveled so that the probe 3 is oriented at a convenient angle. For example, the operator may wish to steady his or her hand on the patient's leg, in which case the probe is swiveled downwards. The illustrated device includes a small LCD screen 2 to display the imagery, and the figure also illustrates a likely point 4 where a catheter may be inserted.

Figure 5:
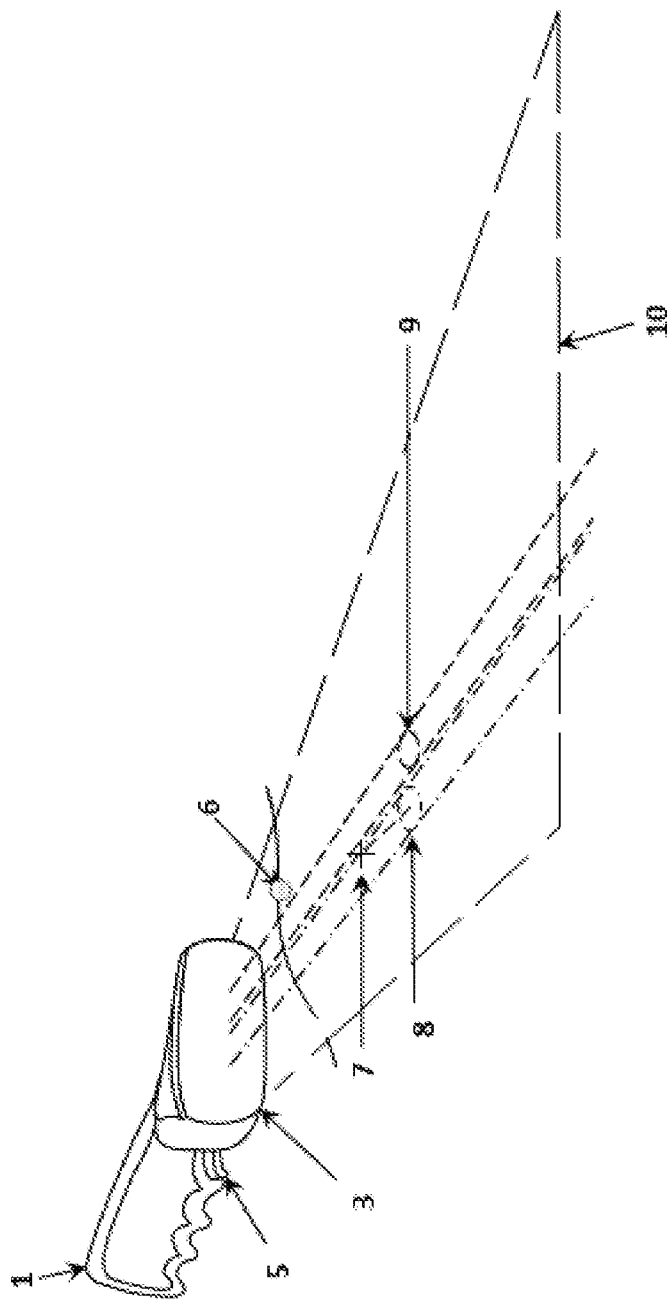
FIG. 5 illustrates a B-mode plane intersecting vein and artery according to an embodiment of the invention.

FIG. 5 illustrates a B-mode plane intersecting a vein and an artery according to at least one embodiment of the invention. FIG. 5 illustrates how the ultrasonic (B-mode) beam 10 would intersect vessels 8 and 9, possibly being a vein and an artery, respectively, pointing downwards from the line between the right leg and the pelvis 6. A trigger 5 on the pistol grip 1 can conveniently turn the beam on when pressed. In at least one embodiment, the probe head 3 is a phase array suitable for B-mode examination.

In addition to the ultrasonic probe and image processing, a controllable laser targeting subsystem using a small light emitting device (or laser) can be provided which illuminates a spot for incision, for example on the groin, where best to insert the surgical instruments (e.g., as illustrated above in FIG. 4) based on ultrasonic imagery.

Figure 6:
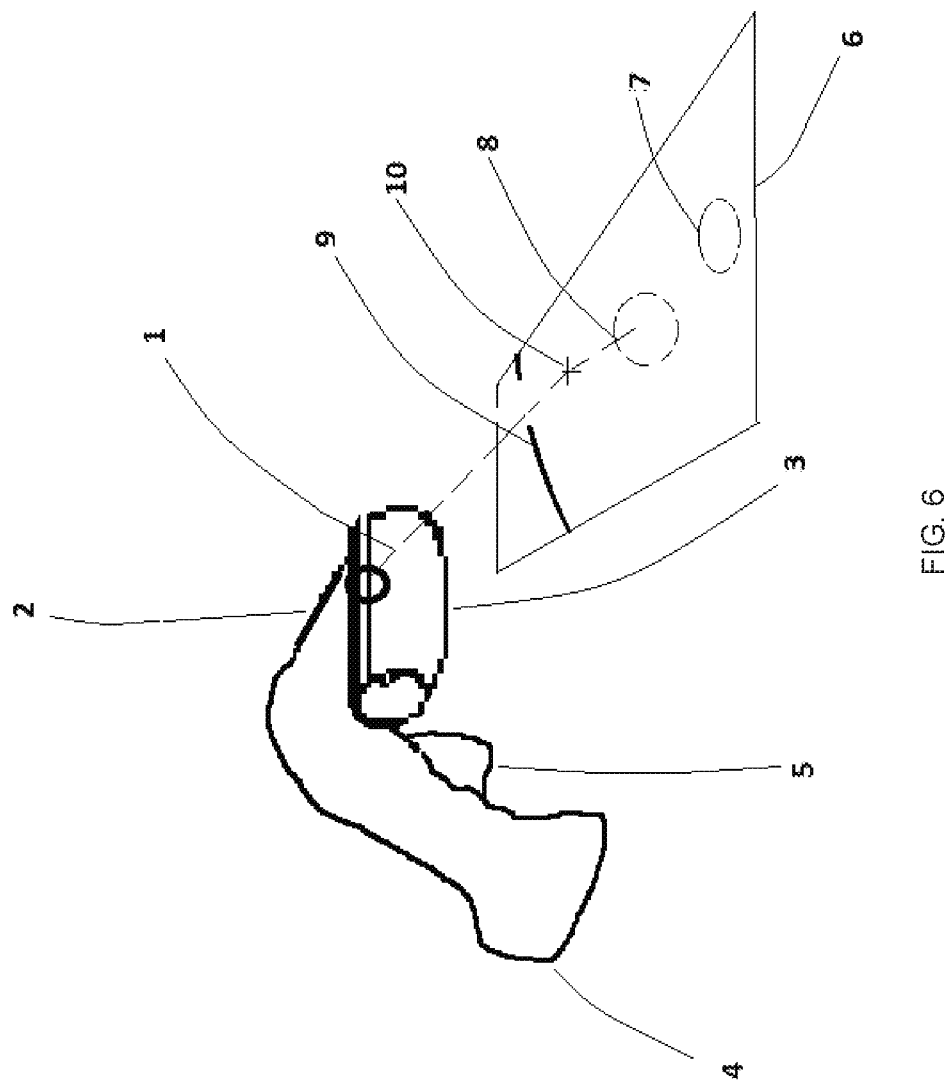
FIG. 6 illustrates a laser targeting system mounted on an instrument according to an embodiment of the invention.

FIG. 6 illustrates a laser targeting system on an instrument according to an embodiment of the invention. This configuration has a laser beam aimed at the insertion point, shown as a dashed line emanating from a small laser with controlled pointing direction. The small circle is the laser's opening. As shown in FIG. 6, the imager and laser can be offset in angle somewhat from the normal entry angle of a needle and catheter, which can be about 30 degrees from the patient's midline in supine position. Thus, the axes of the device could be at 15 to 20 degrees, or alternatively about 40 to 90 degrees. At lower angles, the instrument can be steadied against the patient, but the laser beam may not be much lower so that the targeting spot can be accurately placed. The angle between the probe and the pistol grip can be adjustable for a patient in a sitting position. A system configuration is illustrated in FIG. 6, wherein the ultrasonic probe (3) is shown just above two vessels (7) and (8). A beam (11) can be directed toward the point on the skin (12); and, a pistol grip (13) can be provided to firmly hold the device against the patient's skin.

Figure 7:
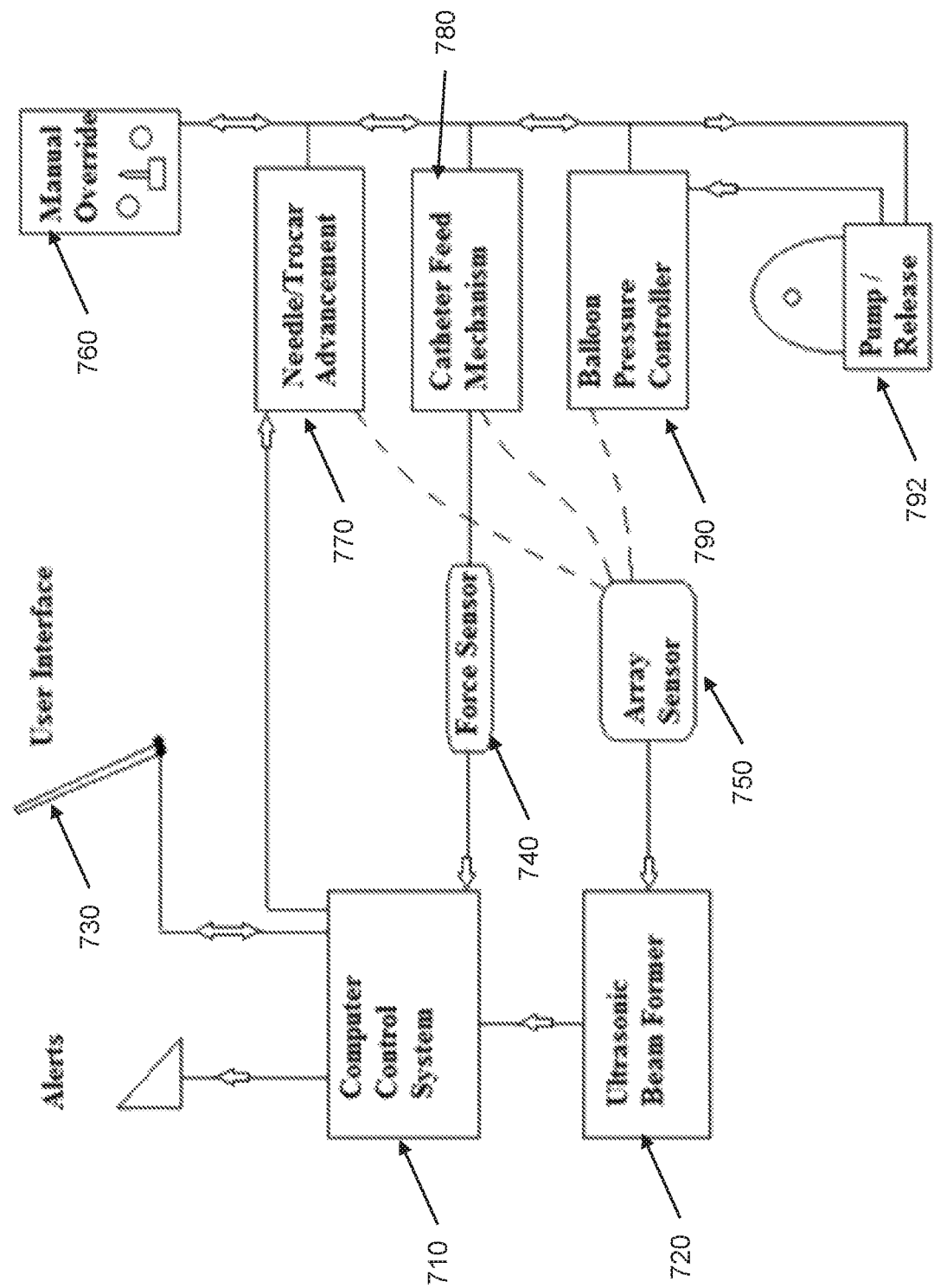
FIG. 7 illustrates a system block diagram according to an embodiment of the invention.

FIG. 7 illustrates a system block diagram according to an embodiment of the invention, wherein the ultrasonic and laser systems are shown to the left in the context of other possible mechanisms. More specifically, an ultrasonic beam former 720 is electrically connected to a computer controller 710 and an array sensor (e.g., phased array) 750. There can be manual overrides to these external systems. The system further includes a manual override 760 electrically connected to a needle/trocar advancement 770, a catheter feed mechanism 780, a balloon pressure controller 790 and a pump/release 792. The system in at least one embodiment also includes a user interface (small screen on the instrument). More specifically, the array sensor 750 is electrically connected to the needle/trocar advancement 770, the catheter feed mechanism 780, and the balloon pressure controller 790. The user interface 730 is electrically connected to the computer controller 710. The computer controller 710 is electrically connected to the needle/trocar advancement 770, a force sensor 740, and the ultrasonic beam former 720. The force sensor 740 are electrically connected to the needle/trocar advancement 770 and the catheter feed mechanism 780, respectively.

Figure 8:
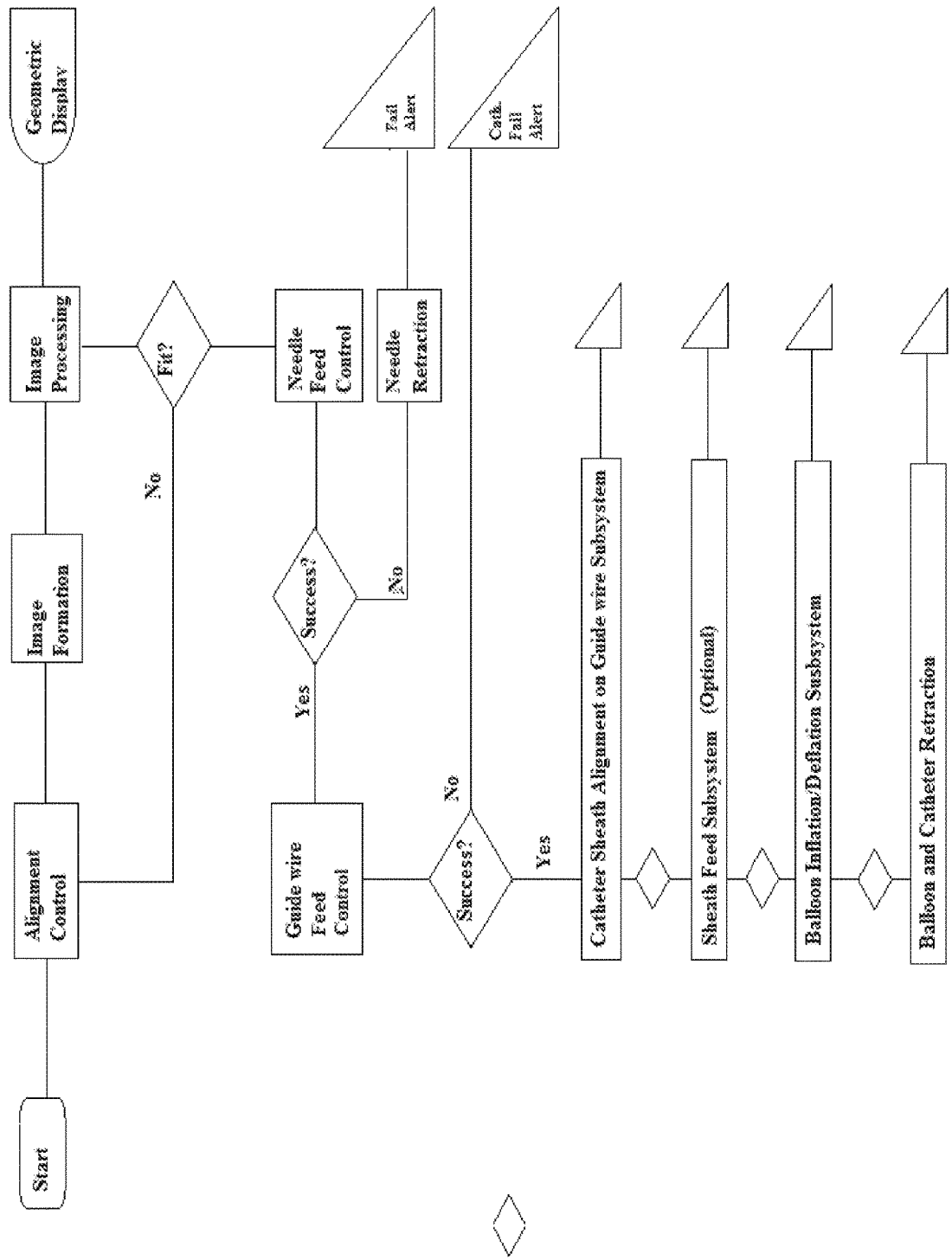
FIG. 8 illustrates an algorithm flow diagram according to an embodiment of the invention.

FIG. 8 illustrates an algorithm flow diagram according to an embodiment of the invention, wherein an ultrasonic phased array sensor mounted on the platform along with a laser targeting system guides several stages of REBOA operation shown here. A "Start" can indicate the result of a trigger or button actuation to start the system. There can be an alignment control algorithm for the laser, which can work together with image processing to guide the operator to a correct fit. If the fit is not achieved at first or during the insertion of the needle, the system can alert the user to incorrect positioning.

Later stages are shown in FIG. 8 to illustrate the operations described above. The later stages can include functions involved with the catheterization discussed above in the context of the overall operation. Various subroutines of the processing can be specialized to particular types of imagery as obtained, for example, by catheter sheath alignment. Balloon and catheter retraction can be monitored by the ultrasonic component, and error signals can be emitted when the vessel is excessively pulled or distorted at the entrance point as monitored by the ultrasonic system and specialized image interpretation algorithm. At insertion and retraction, it is possible that significant blood pooling can be detected.

As the catheter tip approaches the probable location of the outer vessel wall, the associated imaging system can prepare cross-sectional still images about once every millimeter of advance. Distance to the vessel wall can be determined and it can be ensured that the axis is through the vessel center.

As the needle penetrates the vessel, there may be some deformation of the vessel wall. If the deformation indicates that the needle has not penetrated or has missed the vessel, it can be retracted somewhat; and, an error signal can be generated by the device. It is possible that a different needle diameter is needed. An 18-gauge needle may be used for the REBOA system.

If the tip penetrates the vessel wall, the operator can continue by feeding a guide wire into the vessel through the needle. Once the guide wire is in place, a sheath can be inserted without ultrasonic guidance. As the catheter or preceding sheath insertion continues into the vessel, a check can be made by the medical personnel of the insertion force. If the force becomes greater than a set value, then insertion may stop. At this point, a sonographer may examine the progress of the catheter to determine what obstruction has been encountered.

In at least one embodiment of the invention, the beam controller algorithm computes the geometric transform from the central point in the vessel lumen, obtained by imaging means, to position and orient the laser beam(s). The laser controller can solve a high-speed tracking problem where there is wiggling of the operator's hand as well as movement of the patient (e.g., patient gasping). There can also be five degrees of freedom of the device relative to a fixed reference point on the patient (arbitrary) but two more degrees of patient orientation relative to this point's coordinates. Thus, a tracker for seven degrees of freedom at about 10 Hertz frame rate may be used. Given an imaging device with automated designation of the lumen of a vessel, there may be significant error in locating the vessel center from time to time due to imaging artifacts, pulsing arteries, compressing and expanding veins, and/or many other purely computer image extraction variabilities, including various types of noise in the imagery. The needle may be aimed fairly accurately so it will not glance off the outer vessel wall. The tracking algorithm can accommodate large jumps in signal parameters from the imaging sensor, and slower changes in the estimated position of the laser. Additional problems may arise while considering that tracking the current laser position and orientation can be best accomplished by a small accelerometer, but these instruments can drift over time as they may only integrate accelerations in position and orientation changes over time (which are second derivatives). Significantly more error can naturally accumulate in noisier measurements than would be obtained, for example, by a radio transponder between fixed antenna and an antenna on the laser. A direction orientation-detecting gyroscope may be fixed relative to the laser barrel. The latter methods may be considered too bulky and inconvenient; and as such, limiting the design to a miniature accelerometer may require a means to calibrate the first location and orientation, from which to, rather than the actual positions and angles themselves. This can be one of the functions of the ultrasonics subsystem, which can verify the position of the vessel in absolute coordinates. The imaging device may not necessarily detect the orientation and position of the skin over the vessel on which the light spot will appear.

The tracking algorithm can automatically adjust the laser beam so that it is pointing through the center of a cross-section of a vessel obtained by the imager or some such reference point on the vessel. The accuracy of designation can be increased at increased angles of the laser relative to the skin. As illustrated in FIG. 3, the laser and probe are more or less in co-alignment in at least one embodiment.

Again, as the cutting instrument (e.g., a needle or a trocar) penetrates the selected vessel, there may be some deformation of the vessel wall. Arteries tend to be stiffer than veins. In any case, the deformation, if large enough, may indicate that the needle has not penetrated or has missed the vessel. An error signal can be generated by the device, at which point the operator may retract the needle somewhat. The algorithm can use this deformation information to provide an updated image, showing where the needle previously entered but missed.

If the tip penetrates the vessel wall, the imagery can clearly show the needle location as the operator commences feeding a guide wire into the vessel through the needle. Initially, the imagery can be used to check if the wire is following the vessel's lumen and that little force is being applied. Visual verification can be sufficient, but if not, in austere or distracting situations, a warning signal can be emitted if the guide wire fails to negotiate the corner between the needle and the vessel or is otherwise impeded. The intention of all stages of the algorithm can be to reduce chances of failed insertions by any number of causes.

Where a catheter sheath (e.g., a short tube to guide the catheter) is inserted into the vessel prior to the catheter itself to guide it, a check can be made to ensure that the sheath is entering the vessel properly. Again, if the imagery shows a possible missed insertion, a signal can be emitted so that the operator can choose to stop the progress of the insertion.

In at least one embodiment, blood flow at the insertion point is measured in a Doppler mode providing additional evidence to the rule-based system that the vessel is indeed an artery in the case of balloon catheter insertion, or a vein in the case of central line insertion.

Following additional rule-based decisions, the probe and algorithm can continue to monitor the region of the vessel(s) to locate excessive bleeding around the incision in the vessel. If inferred to be dangerous, a signal can be emitted to alert the practitioner. A small surgery can be performed to close the wound; and, re-insertion at a different point may then be attempted.

In all predictions by the system, if there is significant uncertainty as to whether the target vessel is identified by the vessel image processing system, additional warning signals may be generated. These may be signaled to the operator by an audio alert and/or a color code scheme on the screen, such as green for reasonable certainty that the prediction is good, yellow that it is somewhat uncertain, and red that the system is very uncertain and no decisions should be based on system outputs. The signals may maximize the safety of the procedure.

Again at the end of the procedure, the bleeding can be stemmed through the hole in the vessel. With some vessels at accessible points, it may be possible to apply temporary pressure to temporarily restrict blood flow while the catheter is withdrawn. The complete operational package could include a clamping device to prevent further blood loss.

In a REBOA deployment according to an embodiment of the invention, the guide wire is inserted through the needle, the needle is removed while leaving the wire in place, a portion of the algorithm provides special processing which highlights on the screen, and the tip of the needle is withdrawn while clearly distinguishing the needle from the wire (both may look very similar under ultrasound).

The imagery can be displayed on a small computer screen on or near the hand-held unit. It is not required that the imagery is of very high resolution since the algorithm can perform much of the work of locating the vessels and highlighting their outlines or otherwise cueing the operator. Thus, the system can provide robustness of use in an austere environment.

With various trauma cases, it can be important to slow down the rate of blood loss to a body area as rapidly as possible. This includes excessive external bleeding as well as internal hemorrhage. The system can generate segmentations of sonographic imagery to rapidly signal various fingers, motors, and controllers. This imagery may also be displayed to aid technicians in making diagnostic decisions in sometimes inconvenient or distracting circumstances as encountered in the military field or civilian emergency operations.

The system can be portable, unlike current bed-side devices which must be supported by stands or carts near a patient's bedside in an intensive care unit, for example. The system can also provide instant recording of user-selected imagery for later analysis. Some imagery may be difficult to interpret by all but the most experienced personnel. In these circumstances, the imagery can be transmitted via wireless or other network to a doctor or other medic who specializes in the interpretation of sonograms.

At least one embodiment of the invention provides a computer pattern recognition algorithm that identifies arteries in various body areas, including extremities, groin, abdomen, thorax, internal jugular vein, and head. The system also provides automatic control of catheterization through ultrasonic imaging, providing for greater accuracy and rapidity of catheterization.

As will be appreciated by one skilled in the art, aspects of the present invention may be embodied as a system, method or computer program product. Accordingly, aspects of the present invention may take the form of an entirely hardware embodiment or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Figure 9:
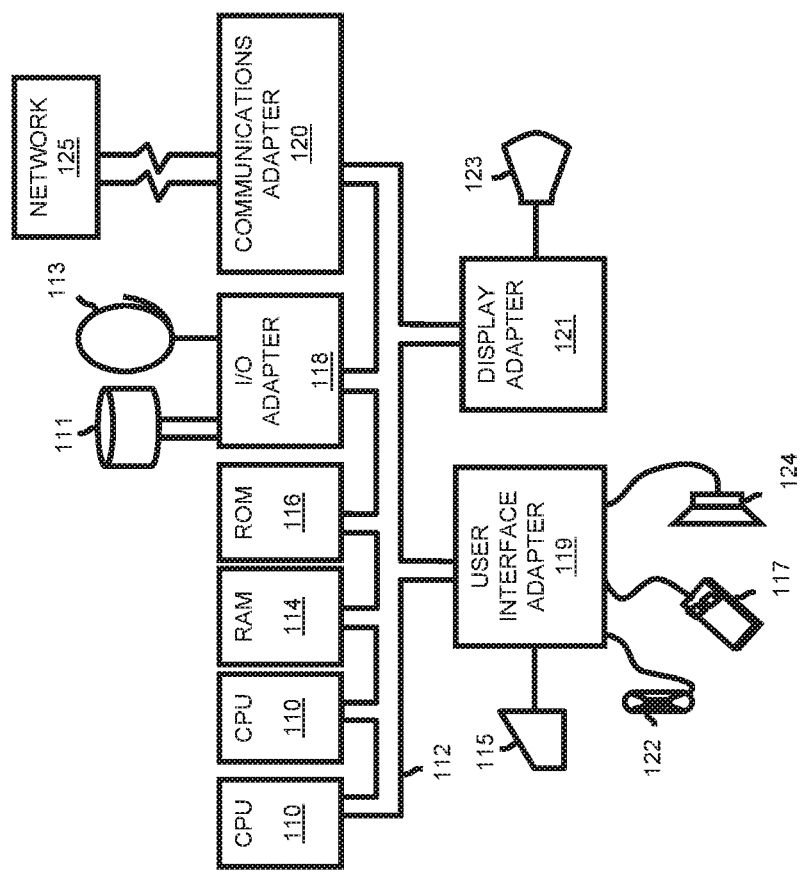
FIG. 9 illustrates a computer program product according to an embodiment of the invention.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. Referring now to FIG. 9, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 110. The CPUs 110 are interconnected with system bus 112 to various devices such as a random access memory (RAM) 114, read-only memory (ROM) 116, and an input/output (I/O) adapter 118. The I/O adapter 118 can connect to peripheral devices, such as disk units 111 and tape drives 113, or other program storage devices that are readable by the system. The system can read the inventive instructions on the program storage devices and follow these instructions to execute the methodology of at least one embodiment of the invention. The system further includes a user interface adapter 119 that connects a keyboard 115, mouse 117, speaker 124, microphone 122, and/or other user interface devices such as a touch screen device (not shown) to the bus 112 to gather user input. Additionally, a communication adapter 120 connects the bus 112 to a data processing network 125, and a display adapter 121 connects the bus 112 to a display device 123 which may be embodied as an output device such as a monitor, printer, or transmitter, for example.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof. The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

INDUSTRIAL APPLICABILITY

A vascular targeting system is provided where the provided systems and methods are particularly suited for obtaining ultrasonic images of a vessel, puncturing an identified center of the vessel, and inserting and maneuvering a guide wire in the vessel with ultrasonic feedback control. A catheter sheath can be inserted over the guide wire and maneuvered with ultrasonic feedback control; and, a catheter can be inserted into the catheter sheath and maneuvered with ultrasonic feedback control.

The system can be used to more rapidly train new technicians, without the current intensive attention of an instructor. Moreover, the system may be configured for numerous other procedures, such as, for example, insertion of chest drains, central venous catheters, insertion of PEG tubes, pacemaker leads, and other critical procedures. The system can be used in the following targeted bleeding areas: Iliac artery proximal to the iliac bifurcation, major artery in upper arm, suprapubic artery (for abdominal hemorrhage), and subxyphoid artery (for control of bleeding in and around the pericardium).

What is claimed is:

1. A method comprising:
    obtaining ultrasonic images of a vessel to be catheterized with an ultrasonic imaging device;
    identifying a center of the vessel using the ultrasonic images from the ultrasonic imaging device, the center of the vessel being identified automatically by a processor;
    emitting a laser onto a skin surface of an appendage to designate a puncture point for a needle, wherein a position of the puncture point is based on said identifying of the center of the vessel;
    puncturing the vessel with the needle based on said identifying of the center of the vessel;

inserting a guide wire into the vessel and maneuvering the guide wire with guide wire ultrasonic feedback control, said guide wire ultrasonic feedback control including:
obtaining ultrasonic images of the vessel and the guide wire in the vessel, and
displaying the ultrasonic images of the vessel and the guide wire in the vessel to a user;
inserting a catheter sheath over the guide wire and maneuvering the catheter sheath with sheath ultrasonic feedback control, said sheath ultrasonic feedback control including:
obtaining ultrasonic images of the vessel and the catheter sheath in the vessel, and
displaying the ultrasonic images of the vessel and the catheter sheath in the vessel to the user;
removing the guide wire; and
inserting a catheter into the catheter sheath and maneuvering the catheter with catheter ultrasonic feedback control, said catheter ultrasonic feedback control including:
obtaining ultrasonic images of the vessel and the catheter in the vessel,
displaying the ultrasonic images of the vessel and the catheter in the vessel to a user,
identifying, via analyzing the ultrasonic images by the processor, when the catheter reaches a predetermined distance from the puncture point, and
automatically inflating by the processor a balloon of the catheter in response to the catheter reaching the predetermined distance from the puncture point.

2. The method according to claim 1, further comprising:
measuring a rate of blood flow in the vessel; and
adjusting an amount of air in a balloon of the catheter with the processor based on the measured blood flow.

3. A system comprising:
a handheld probe configured to obtain ultrasonic images of a vessel to be catheterized and ultrasonic images of a catheter in the vessel, and at least one of ultrasonic images of a guidewire in the vessel, ultrasonic images of a catheter sheath in the vessel;
a laser device configured to emit a laser;
a display connected to said handheld probe, said display displaying the ultrasonic images; and
a computer control device having processing circuitry configured to
automatically identify a center of the vessel using the ultrasonic images from the ultrasonic imaging device,
control the laser device to emit a laser onto a skin surface of an appendage to designate a puncture point for a needle, a position of the puncture point being based on said identifying of the center of the vessel,
identify, via analyzing ultrasonic images of the vessel and a catheter obtained when the vessel is punctured with the needle and the catheter is inserted into a catheter sheath and maneuvered with catheter ultrasonic feedback control, when the catheter reaches a predetermined distance from the puncture point,
automatically inflate a balloon of the catheter in response to the catheter reaching the predetermined distance from the puncture point, and
display on the display the ultrasonic images of the vessel and the catheter in the vessel to a user.

4. The system according to claim 3, further comprising:
a laser pointer for emitting a laser onto a skin surface of the appendage to designate a puncture point for a needle, wherein a position of the puncture point is based on the identification of the center of the vessel.

5. The system according to claim 3, wherein said processing circuitry or performs at least one of:
adjusting an amount of air in a balloon of the catheter based on measured blood flow; or
automatically analyzing the ultrasonic images to measure a distance between a tip of at least one of the guide wire, the catheter, and the sheath and a vessel wall of the vessel, said processor generates an alert when the measured distance between the tip and the vessel wall falls below a threshold distance.

6. The system according to claim 3, wherein said processing circuitry
automatically analyzes the ultrasonic images to measure a distance between a balloon of the catheter and a vessel wall of the vessel, and
generates an alert when the measured distance between the balloon and the vessel wall falls below a threshold distance.

7. The system according to claim 3, further comprising:
a needle configured to puncture the vessel based on the identification of the center of the vessel by the processing circuitry;
said guidewire, said guidewire configured to be inserted into the vessel and maneuvered with guidewire ultrasonic feedback control, the guidewire ultrasonic feedback control including ultrasonic images of the vessel and the guidewire in the vessel;
said catheter sheath, said catheter sheath configured to be inserted over the guidewire and maneuvered with sheath ultrasonic feedback control, said sheath ultrasonic feedback control including ultrasonic images of the vessel and said catheter sheath in the vessel;
said catheter, said catheter configured to be inserted into the catheter sheath and maneuvered with catheter ultrasonic feedback control, said catheter ultrasonic feedback control including ultrasonic images of the vessel and said catheter in the vessel.

8. A method comprising:
obtaining ultrasonic images of a vessel to be catheterized with an ultrasonic imaging device;
identifying a center of the vessel using the ultrasonic images from the ultrasonic imaging device, the center of the vessel being identified with a processor;
illuminating a spot on the skin by a directable laser where the needle can be inserted;
aligning the needle in parallel with the laser's bean;
puncturing the vessel with the needle based on said identifying of the center of the vessel;
inserting a guide wire into the vessel and maneuvering the guide wire with guide wire ultrasonic feedback control, said guide wire ultrasonic feedback control including:
obtaining ultrasonic images of the vessel and the guide wire in the vessel, and
displaying the ultrasonic images of the vessel and the guide wire in the vessel to a user;
inserting a catheter sheath over the guide wire and maneuvering the catheter sheath with sheath ultrasonic feedback control, said sheath ultrasonic feedback control including:
obtaining ultrasonic images of the vessel and the catheter sheath in the vessel, and
displaying the ultrasonic images of the vessel and the catheter sheath in the vessel to the user;
removing the guide wire; and inserting a catheter into the catheter sheath and maneuvering the catheter with catheter ultrasonic feedback control, said catheter ultrasonic feedback control including:
- obtaining ultrasonic images of the vessel and the catheter in the vessel,
- displaying the ultrasonic images of the vessel and the catheter in the vessel to a user,
- identifying, via analyzing the ultrasonic images by the processor, when the catheter reaches a predetermined distance from the puncture point, and
- automatically inflating by the processor a balloon of the catheter in response to the catheter reaching the predetermined distance from the puncture point.

9. The method according to claim 8, wherein the illuminating a spot on the skin is by a laser mounted in fixed position relative to the ultrasound beam, and which swivels allowing the laser to be directed by motors at a spot on the skin where a needle should be inserted.

10. The method according to claim 8, further comprising:
controlling direction angles of the laser with motors which aim the laser's beam at the interior of the selected vessel at the plane of the cross-section.

11. The method according to claim 10, wherein the controlling of direction angles of the laser is by software which control motors.

12. The method further according to claim 11, wherein the software computes the angles by which the motors should direct the laser, and converts the computations from digital form to analog form suitable to drive the motors.

13. The method according to claim 12, wherein the motors are linear motors.

14. The method further according to claim 10, wherein the motors are Selsin motors.

15. The method further according to claim 14, wherein the imaged vessel is determined to be a vein when the imaged vessel is compressed.

16. The method further according to claim 14, wherein the imaged vessel is determined to be an artery when the imaged vessel is not compressed.

17. The method further according to claim 8, further comprising:
initiating location of arteries and/or veins by intersecting horizontal and vertical lines through peaks of histogram intensities, wherein a horizontal line passes through the peak of a histogram, latter summing image intensities across each row; and a vertical line passes through a peak in the marginal histogram which sums intensities across each column of the image.

18. The method further according to claim 17, wherein diagonal lines are intersected with the vertical and horizontal lines, wherein the diagonal lines pass through the histogram which sums image intensities along each diagonal line.

19. The method further according to claim 8, further comprising:
determining which candidate intersections of the lines are one of several combinations occurring in a groin area selected from a group consisting of:
vein and artery,
two veins and one artery,
one vein and two arteries, and
two veins and two arteries,
wherein all being possible identifications by the imaging algorithm depending on how far above or below the groin crease, the interlingual crease, the user has placed the ultrasonic probe.

20. The method further according to claim 8, wherein the locations used to direct the user to move the probe upwards, toward the head, or downwards; since the both artery and vein have bifurcations near the crease, whereas it is desired to insert the needle or trocar into the vessel above its bifurcation to allow ease of insertion of the catheter.

* * * * *